United States Patent
Jung

(10) Patent No.: US 6,413,405 B1
(45) Date of Patent: Jul. 2, 2002

(54) ACTIVE CARBON ELECTRO-DEPOSITED WITH AG-I SYSTEM HAVING STERILIZING EFFECT

(75) Inventor: Woo Young Jung, Chung-Ju (KR)

(73) Assignee: Sol Nanochem Ltd. (KR)

( * ) Notice: Subject to any disclaimer, the term of this patent is extended or adjusted under 35 U.S.C. 154(b) by 0 days.

(21) Appl. No.: 09/719,700

(22) PCT Filed: Jul. 21, 1999

(86) PCT No.: PCT/KR99/00386
§ 371 (c)(1),
(2), (4) Date: Dec. 14, 2000

(87) PCT Pub. No.: WO00/63465
PCT Pub. Date: Oct. 26, 2000

(30) Foreign Application Priority Data

Apr. 15, 1999 (KR) .............................. 99/13302

(51) Int. Cl.[7] .............................. C25D 5/10; C25D 5/54; C25D 5/34
(52) U.S. Cl. ..................... 205/170; 205/159; 205/219
(58) Field of Search ................. 205/159, 219, 205/316, 170; 428/696

(56) References Cited

FOREIGN PATENT DOCUMENTS

CN          1103054    *  5/1995

OTHER PUBLICATIONS

Ehrburger et al., "Adsorption and Decomposition of Silver. Complexes on Carbons", Extr. Abstr. Program—Bienn. Conf. Carbon, 16th, pp. 347–348, (no month available) 1983.*

Andrzejak et al., "Electrocatalytic Properties of Active Carbon with Deposited Silver", Chem. Stasow, vol. 21, Nos. 3–4, pp. 441–445, (no month available) 1977.*
Gamburtsev et al., "Study of Catalysts for the Electrchemical Reduction of Oxygen. I. Preparation and Characteristics of the Silver–Active Carbon Catalyst for Oxygen Gas–Diffusion Electrodes Operating with an Alkaline Electrolyte", Izw. Khim., vol. 8, No. 3, (no month available) 1975.*
Egorov et al., "Metallized Activated Carbon for Purification of Vodka", Otkrytiya, Izobret., Prom. Obraztsy, Tovarnye Znaki, vol. 47, No. 25, pp. 13, (no month available) 1970.*
Kuzin, "Production of Metallized Active Carbons", Zh. Prikl. Khim. (Leningrad), vol. 43, No. 10, pp. 2341–2343, (no month available) 1970.*
References U, V and W were cited on the International Search Report. None of these references were considered because there were no copies of them in the application.*
** Abstract only.*

* cited by examiner

Primary Examiner—Edna Wong
(74) Attorney, Agent, or Firm—Webb Ziesenheim Logsdon Orkin & Hanson, P.C.

(57) ABSTRACT

An environmentally functional active carbon and its method of manufacturing is provided. The active carbon has improved adsorption capability against disease-source bacteria and microbes with prominent anti-bacterial and sterilizing effect as well as against organic and inorganic contaminants due to the process of electro-depositing Ag—I to the surface of active carbon and active carbon fiber. This invention creates functional active carbon having outstanding sterilizing effect for disease-source bacteria from known bacteria such as Gram positive bacteria including *Staphylococcus, Bacillus subtillis* and Gram negative bacteria including *Escherichia coli, Pseudomonas Aeruginosa, Klebsiella Pneumonie, Candida Albicans* causing albicans as yeast fungus, Trichophyton interdigital causing athlete's foot as a kind of mold.

6 Claims, 6 Drawing Sheets

ACTIVE CARBON ELECTRO-DEPOSITED WITH AG-I SYSTEM HAVING STERILIZING EFFECT

BACKGROUND OF THE INVENTION

1. Field of the Invention

This invention relates to active carbon electro-deposited with Ag—I compositions having a sterilizing effect and a method of preparing such compositions.

2. Background Art

Plating a metal element on an adsorbent increase the selective adsorption capability of the adsorbent owing to the surface polarity of the metal ion while maintaining a high level of adsorption capability. It is applied to remove polar contaminants from polluted water and wastewater. Known methods of metal impregnation for solid substrates are dipping, chemical vapor deposition and admixing during the manufacture process. Recently, much of research and development is being done concerning the anti-bacterial effect of active carbon electro-deposited with Ag. However, so far there has been no report about the anti-bacterial and sterilizing effect of active carbon electro-deposited with Ag—I against disease-source bacteria.

DISCLOSURE OF THE INVENTION

The purpose of this invention is to provide functional active carbon having improved adsorption capability against disease-source bacteria and microbes with prominent anti-bacterial and sterilizing effect as well as against organic and inorganic contaminants and preparing method thereof. As used herein, the term "active carbon" is meant to include activated carbon.

According to the present invention, there is provided a method for preparing active carbon electro-deposited with Ag—I having sterilizing and anti-bacteria effect comprising:

1) a step of applying electric current to active carbon in an Ag plating bath containing Ag salt solution in the plating bath;
2) a step of washing and drying the active carbon of step 1); and
3) a step of applying electric current to the washed and dried active carbon in a Iodine plating bath containing Iodine salt solution.

Active carbon in this invention means powdered active carbon, granular active carbon and active carbon fiber. Active carbon fiber can be woven into filter cloths.

For this invention, $AgNO_3$, $CH_3CO_2Ag$ and $AgCN$ for silver salt, $KIO_3$ and $NaIO_3$ for iodine salt can be used.

It is desirable to use 1~10 wt % concentration of silver salt in the silver plating bath. If the concentration is less than 1 wt %, there is insufficient amount of silver on the surface of active carbon since the dissociated electrolyte concentration is low in electro-depositing. If it is more than 10 wt %, there happens silver sedimentation correlatively in electrolyte since dissociated electrolyte concentration is high. Therefore, adsorption capability is decreased because carbon surface structure is changed.

It is desirable to use 5 wt %~30 wt % concentration of electro-deposited solution for iodine composition. If this concentration is less than 5 wt %, there is insufficient amount of silver on the surface of active carbon since dissociated electrolyte concentration is low in electro-depositing. If it is more than 30 wt %, the surface structure of active carbon is changed and adsorption capability is decreased because dissociated electrolyte concentration is high.

It is desirable to use 1 V~50 V for this invention. If the voltage is lower than 1 V, there is less content of silver and iodine on the surface of active carbon because dissociated electrolyte concentration is low in electro-depositing. If it is more than 50 V, there happens sedimentation correlatively in electrolyte because dissociated electrolyte concentration is high. It changes the surface structure of active carbon, and then makes adsorption capability decrease.

It is desirable to use 0.1 A~5.0 A electric current intensity for this invention. If the current intensity is lower than 0.1 A, there is less content of silver and iodine on the surface of active carbon because dissociated electrolyte concentration is low in electro-depositing. If it is more than 5.0 A, there happens sedimentation correlatively in electrolyte because dissociated electrolyte concentration is high. It changes the surface structure of active carbon, and then makes adsorption capability decrease.

It is desirable to apply 10–120 seconds of electric current for this invention. If it takes less than 10 seconds, there is less content of silver and iodine on the surface of active carbon because dissociated electrolyte concentration is low in electro-depositing. If it takes more than 120 seconds, there happens sedimentation correlatively in electrolyte because dissociated electrolyte concentration is high. It changes the surface structure of active carbon, and then makes adsorption capability decrease.

Target microorganisms for anti-bacteria and sterilizing are mainly disease-source bacteria as described below. Some bacteria are used for standard resistance test against microbes in anti-bacteria-treated products in Korea, U.S.A and Japan.

1) Disease-source Bacteria a. *Staphylococcus Aureus*: This is spread widely in natural world and causes yellow suppuration in the skin and food poisoning when food is contaminated by it. This bacterium is found in skin, mucous membrane, air, water, milk, etc. It is known as the origin of bacteria induced odor like rotten smell and sweat smell.

b. *Proteus Vulgalis*: This is bacterium to decompose protein and urea and is a kind of intestinal bacterium, which generates ammonia by decomposing urea rapidly. It decomposes urea and generates ammonia from wet-napkin of baby and then cause eczema in the soft skin of baby.

c. *Escherichia Coli, E. Coli* O-16: This is a representative bacterium living in intestines of man or animal, which contaminates water, soil and food. This bacteria usually do not have characteristic of disease-source, but it is contaminated by excrement directly or indirectly while it is living in food or beverages. So it is used as an index of contamination possibility of *Salmonella typni, Shigella dysenteriae* of disease-source intestinal bacteria.

d. *Pseudomonas Aeruginosa*: This causes green excrement of infant or green milk of woman in childbed, which is usually coloring bacteria into green and cause inflammation in bronchus, meninges, eye, nose, ear, etc.

e. *Klebsiella Pneumoniae* f. *Salmonella Choleraesuis* g. *Salmonella Typni* h. *Salmonella Enteritidis* i. *Shigella Dysenteriae* j. *Clostridium Tentani*

2) Filamentous Fungus
a. *Trichophyton Mentagrophtes*
b. *Candina Albicans*: This causes candidiasis, which generates skin disease by decomposing urea into ammonia
c. *Penucillum Luteum*
d. *Micrococcus Gyseum*

Mode for Carrying out the Inventions

The following examples have been carried out in regard to anti-bacteria and sterilizing effect of active carbon electro-deposited with Ag—I system using standard disease-source bacteria, such as Gram positive bacteria of Staphylococcus, *Bacillus Subtillis*, and Gram negative bacteria of *Escherichia Coli, Pseudomonas aeruginosa, Klebsiella Pneumoniae, Candida Albicans* causing condidiasis as yeast fungus, and Trichophyton Interdigital causing athlete's foot as a kind of mold.

EXAMPLE 1

Active carbon for liquid phase (1560 m'/g, 8×12 mesh size, produced by Dong-Yang Carbon Co., Ltd. of Korea ) is used to produce functional active carbon having anti-bacteria and sterilizing effect by electro depositing active carbon with Ag—I.

For silver plating, 1 wt % $AgNO_3$ solution is used as electrolyte. Active carbon is plated under the condition of 1 V voltage and 0.1 A electric current for about 10 seconds at room temperature. Active carbon obtained from the above treatment is dried at 80° C. in the oven for a day.

Electricity, 1 V voltage and 0.1 A current in the 15 wt % $NaIO_3$ solution for about 60 seconds is applied again to the copper plated active carbon. Finally, functionally active carbon plated with Ag—I having anti-bacteria and sterilizing effect is produced.

Functionally active carbon is dried at 80° C. in the oven for a day, after washing 2 or 3 times in the distilled water. Table 1 shows its adsorption characteristic and FIG. 1 shows its anti-bacteria and sterilization characteristic against the disease-source bacteria. As a result, there is no significant change of surface structure such as BET specific surface area and pore volumes. Also there is almost no consequent change in adsorption capability.

However, the present invention brings huge increase in sterilization and anti-bacteria characteristic of active carbon electro-deposited with Ag—I, compared with non-treatment active carbon. This shows that process of active carbon electro-deposited with Ag—I performs well sterilization and anti-bacteria function with no significant change of surface structure of active carbon.

EXAMPLE 2

The active carbon used for this example is same as Example 1.

Electrolyte made from 5 wt % of $AgNO_3$ solution is used for silver plating. Active carbon is plated under the condition of 30 V voltage and 3.0 A electric current for about 60 seconds at room temperature. Active carbon obtained from the above treatment is dried at 80° C. in the oven for a day.

Electricity, 30 V voltage and 3.0 A current in the 5 wt % $KIO_3$ solution for about 10 seconds is applied again. Finally, functionally active carbon plated with Ag—I having anti-bacteria and sterilizing effect is produced.

Functionally active carbon is dried at 80° C. in the oven for a day, after washing 2 or 3 times in the distilled water. Table 1 shows its adsorption characteristic and FIG. 2 shows its anti-bacteria and sterilization characteristic against the disease-source bacteria. As a result, there is no significant change of surface structure such as BET specific surface area and pore volumes. Also there is almost no consequent change in adsorption capability.

However, the present invention brings huge increase in sterilization and anti-bacteria characteristic of active carbon electro-deposited with Ag—I, compared with non-treatment active carbon. This shows that process of active carbon electro-deposited with Ag—I performs well sterilization and anti-bacteria function with no significant change of surface structure of active carbon.

EXAMPLE 3

The active carbon used for this example is same as Example 1.

Electrolyte made from 10 wt % of $AgNO_3$ solution is used for silver plating. Active carbon is plated under the condition of 50 V voltage and 5.0 A electric current for about 120 seconds at room temperature. Active carbon obtained from the above treatment is dried at 80° C. in the oven for a day.

Electricity, 50 V voltage and 5.0 A current in the 30 wt % $KIO_3$ solution for about 120 seconds is applied again. Finally, functionally active carbon plated with Ag—I having anti-bacteria and sterilizing effect is produced.

Functionally active carbon is dried at 80° C. in the oven for a day, after washing 2 or 3 times in the distilled water. Table 1 shows its adsorption characteristic and FIG. 3 shows its anti-bacteria and sterilization characteristic against the disease-source bacteria. As a result, there is no significant change of surface structure such as BET specific surface area and pore volumes. Also there is almost no consequent change in adsorption capability.

However, the present invention brings huge increase in sterilization and anti-bacteria characteristic of active carbon electro-deposited with Ag—I, compared with non-treatment active carbon. This shows that process of active carbon electro-deposited with Ag—I performs well sterilization and anti-bacteria function with no significant change of surface structure of active carbon.

EXAMPLE 4

The active-carbon used for this example is same as Example 1.

Electrolyte made from 1 wt % of $CH_3CO_2Ag$ solution is used for silver plating. Active carbon is plated under the condition of 5 V voltage and 0.5 A electric current for about 30 seconds at room temperature. Active carbon obtained from the above treatment is dried at 80° C. in the oven for a day.

Electricity, 5 V voltage and 0.5 A current in the 5 wt % $KIO_3$ solution for about 30 seconds is applied again. Finally, functionally active carbon plated with Ag—I having anti-bacteria and sterilizing effect is produced.

Functionally active carbon is dried at 80 ° C. in the oven for a day, after washing 2 or 3 times in the distilled water. Table 1 shows its adsorption characteristic and FIG. 4 shows its anti-bacteria and sterilization characteristic against the disease-source bacteria. As a result, there is no significant change of surface structure such as BET specific surface area and pore volumes. Also there is almost no consequent change in adsorption capability.

However, the present invention brings huge increase in sterilization and anti-bacteria characteristic of active carbon electro-deposited with Ag—I, compared with non-treatment active carbon. This shows that process of active carbon electro-deposited with Ag—I performs well sterilization and anti-bacteria function with no significant change of surface structure of active carbon.

EXAMPLE 5

The active carbon used for this example is same as Example 1.

Electrolyte made from 5 wt % of $CH_3CO_2Ag$ solution is used for silver plating. Active carbon is plated under the condition of 30 V voltage and 3.0 A electric current for about 45 seconds at room temperature. Active carbon obtained from the above treatment is dried at 80° C. in the oven for a day.

Electricity, 30 V voltage and 0.3 A current in 15 wt % $KIO_3$ solution for about 45 seconds is applied again. Finally, functionally active carbon plated with Ag—I having anti-bacteria and sterilizing effect is produced. Functionally active carbon is dried at 80° C. in the oven for a day, after washing 2 or 3 times in the distilled water. Table 1 shows its adsorption characteristic and FIG. 5 shows its anti-bacteria and sterilization characteristic against the disease-source bacteria. As a result, there is no significant change of surface structure such as BET specific surface area and pore volumes. Also there is almost no consequent change in adsorption capability.

However, the present invention brings huge increase in sterilization and anti-bacteria characteristic of active carbon electro-deposited with Ag—I, compared with non-treatment active carbon. This shows that process of active carbon electro-deposited with Ag—I performs well sterilization and anti-bacteria function with no significant change of surface structure of active carbon.

EXAMPLE 6

The active carbon used for this example is same as Example 1.

Electrolyte made from 10 wt % of $CH_3CO_2Ag$ solution is used for silver plating. Active carbon is plated under the condition of 50 V voltage and 5.0 A electric current for about 90 seconds at room temperature. Active carbon obtained from the above treatment is dried at 80° C. in the oven for a day.

Electricity, 50 V voltage and 5.0 A current in the 30 wt % $NaIO_3$ solution for about 90 seconds is applied again. Finally, functionally active carbon plated with Ag—I having anti-bacteria and sterilizing effect is produced.

Functionally active carbon is dried at 80° C. in the oven for a day, after washing 2 or 3 times in the distilled water. Table 1 shows its adsorption characteristic and FIG. 6 shows its anti-bacteria and sterilization characteristic against the disease-source bacteria. As a result, there is no significant change of surface structure such as BET specific surface area and pore volumes. Also there is almost no consequent change in adsorption capability.

However, the present invention brings huge increase in sterilization and anti-bacteria characteristic of active carbon electro-deposited with Ag—I, compared with non-treatment active carbon. This shows that process of active carbon electro-deposited with Ag—I performs well sterilization and anti-bacteria function with no significant change of surface structure of active carbon.

EXAMPLE 7

The active carbon used for this example is same as Example 1.

Electrolyte made from 1 wt % of AgCN solution is used for silver plating. Active carbon is plated under the condition of 5 V voltage and 0.5 A electric current for about 10 seconds at room temperature. Active carbon obtained from the above treatment is dried at 80° C. in the oven for a day.

Electricity, 5 V voltage and 0.5 A current in the 5 wt % $KIO_3$ solution for about 10 seconds is applied again. Finally, functionally active carbon plated with Ag—I having anti-bacteria and sterilizing effect is produced.

Functionally active carbon is dried at 80° C. in the oven for a day, after washing 2 or 3 times in the distilled water. Table 1 shows its adsorption characteristic and FIG. 7 shows its anti-bacteria and sterilization characteristic against the disease-source bacteria. As a result, there is no significant change of surface structure such as BET specific surface area and pore volumes. Also there is almost no consequent change in adsorption capability.

However, the present invention brings huge increase in sterilization and anti-bacteria characteristic of active carbon electro-deposited with Ag—I, compared with non-treatment active carbon. This shows that process of active carbon electro-deposited with Ag—I performs well sterilization and anti-bacteria function with no significant change of surface structure of active carbon.

EXAMPLE 8

The active carbon used for this example is same as Example 1.

Electrolyte made from 5 wt % of AgCN solution is used for silver plating. Active carbon is plated under the condition of 20 V voltage and 2.0 A electric current for about 45 seconds at room temperature. Active carbon obtained from the above treatment is dried at 80° C. in the oven for a day.

Electricity, 20 V voltage and 2.0 A current in the 10 wt % $NaIO_3$ solution for about 45 seconds is applied again. Finally, functionally active carbon plated with Ag—I having anti-bacteria and sterilizing effect is produced.

Functionally active carbon is dried at 80° C. in the oven for a day, after washing 2 or 3 times in the distilled water. Table 1 shows its adsorption characteristic and FIG. 8 shows its anti-bacteria and sterilization characteristic against the disease-source bacteria. As a result, there is no significant change of surface structure such as BET specific surface area and pore volumes. Also there is almost no consequent change in adsorption capability.

However, the present invention brings huge increase in sterilization and anti-bacteria characteristic of active carbon electro-deposited with Ag—I, compared with non-treatment active carbon. This shows that process of active carbon electro-deposited with Ag—I performs well sterilization and anti-bacteria function with no significant change of surface structure of active carbon.

EXAMPLE 9

The active carbon used for this example is same as Example 1.

Electrolyte made from 10 wt % of AgCN solution is used for silver plating. Active carbon is plated under the condition of 40 V voltage and 4.0 A electric current for about 120 seconds at room temperature. Active carbon obtained from the above treatment is dried at 80° C. in the oven for a day.

Electricity, 40 V voltage and 4.0 A current in the 20 wt % $NaIO_3$ solution for about 120 seconds is applied again. Finally, functionally active carbon plated with Ag—I having anti-bacteria and sterilizing effect is produced.

Functionally active carbon is dried at 80° C. in the to oven for a day, after washing 2 or 3 times in the distilled water. Table 1 shows its adsorption characteristic and FIG. 9 shows its anti-bacteria and sterilization characteristic against the disease-source bacteria. As a result, there is no significant change of surface structure such as BET specific surface area and pore volumes. Also there is almost no consequent change in adsorption capability.

However, the present invention brings huge increase in sterilization and anti-bacteria characteristic of active carbon electro-deposited with Ag—I, compared with non-treatment active carbon. This shows that process of active carbon electro-deposited with Ag—I performs well sterilization and anti-bacteria function with no significant change of surface structure of active carbon.

EXAMPLE 10

Active carbon fiber of Kuraray (Japan) is used as adsorbent for silver plating. 5 wt % $AgNO_3$ solution is used as electrolyte. Active carbon is plated under the condition of 30 V voltage and 3.0 A electric current for about 90 seconds at room temperature. Active carbon obtained from the above treatment is dried at 80° C. in the oven for a day.

Electricity, 30 V voltage and 3.0 A current in the 10 wt % $NaIO_3$ solution for about 90 seconds is applied again. Finally, functionally active carbon plated with Ag—I having anti-bacteria and sterilizing effect is produced.

Functionally active carbon is dried at 80° C. in the oven for a day, after washing 2 or 3 times in the distilled water. Table 1 shows its adsorption characteristic and FIG. 10 shows its anti-bacteria and sterilization characteristic against the disease-source bacteria. As a result, there is no significant change of surface structure such as BET specific surface area and pore volumes. Also there is almost no consequent change in adsorption capability.

However, the present invention brings huge increase in sterilization and anti-bacteria characteristic of active carbon electro-deposited with Ag—I, compared with non-treatment active carbon. This shows that process of active carbon electro-deposited with Ag—I performs well sterilization and anti-bacteria function with no significant change of surface structure of active carbon.

EXAMPLE 11

Active carbon fiber of Kuraray (Japan) is used as adsorbent for silver plating. 10 wt % $CH_3CO_2Ag$ solution is used as electrolyte. Active carbon is plated under the condition of 15 V voltage and 1.5 A electric current for about 120 seconds at room temperature. Active carbon obtained from the above treatment is dried at 80° C. in the oven for a day.

Electricity, 15 V voltage and 1.5 A current in the 20 wt % $NaIO_3$ solution for about 120 seconds is applied again. Finally, functionally active carbon plated with Ag—I having anti-bacteria and sterilizing effect is produced.

Functionally active carbon is dried at 80° C. in the oven for a day, after washing 2 or 3 times in the distilled water. Table 1 shows its adsorption characteristic and FIG. 11 shows its anti-bacteria and sterilization characteristic against the disease-source bacteria. As a result, there is no significant change of surface structure such as BET specific surface area and pore volumes. Also there is almost no consequent change in adsorption capability.

However, the present invention brings huge increase in sterilization and anti-bacteria characteristic of active carbon electro-deposited with Ag—I, compared with non-treatment active carbon. This shows that process of active carbon electro-deposited with Ag—I performs well sterilization and anti-bacteria function with no significant change of surface structure of active carbon.

EXAMPLE 12

Active carbon fiber of Kuraray (Japan) is used as adsorbent for silver plating. 5 wt % AgCN solution is produced to use as electrolyte. Active carbon is plated under the condition of 50 V voltage and 5.0 A electric current for about 30 seconds at room temperature. Active carbon obtained from the above treatment is dried at 80° C. in the oven for a day.

Electricity, 50 V voltage and 5.0 A current in the 30 wt % $KIO_3$ solution for about 30 seconds is applied again. Finally, functionally active carbon plated with Ag—I having anti-bacteria and sterilizing effect is produced.

Functionally active carbon is dried at 80° C. in the oven for a day, after washing 2 or 3 times in the distilled water. Table 1 shows its adsorption characteristic and FIG. 12 shows its anti-bacteria and sterilization characteristic against the disease-source bacteria. As a result, there is no significant change of surface structure such as BET specific surface area and pore volumes. Also there is almost no consequent change in adsorption capability.

However, the present invention brings huge increase in sterilization and anti-bacteria characteristic of active carbon electro-deposited with Ag—I, compared with non-treatment active carbon. This shows that process of active carbon electro-deposited with Ag—I performs well sterilization and anti-bacteria function with no significant change of surface structure of active carbon.

Each active carbon electro-deposited with Ag—I system is washed 2 or 3 times and dried at 100° C. for 12 hours and used. Comparison between the active carbon made from the above examples and non-treated active carbon in pore structure, specific surface area and iodine adsorption capability and Quin tests for anti-bacteria and sterilizing are made as follows, and then the results are illustrated at Table 1 and FIGS. 1 to 12.

BRIEF DESCRIPTION OF THE DRAWINGS

Each active carbon electro-deposited with Ag—I system is washed 2 or 3 times and dried at 100° C. for 12 hours and used. Comparison between the active carbon made from the above examples and non-treated active carbon in pore structure, specific surface area and iodine adsorption capability and Quin tests for anti-bacteria and sterilizing are made as follows, and then the results are illustrated at Table 1 and FIGS. 1 to 12.

Figure 1:
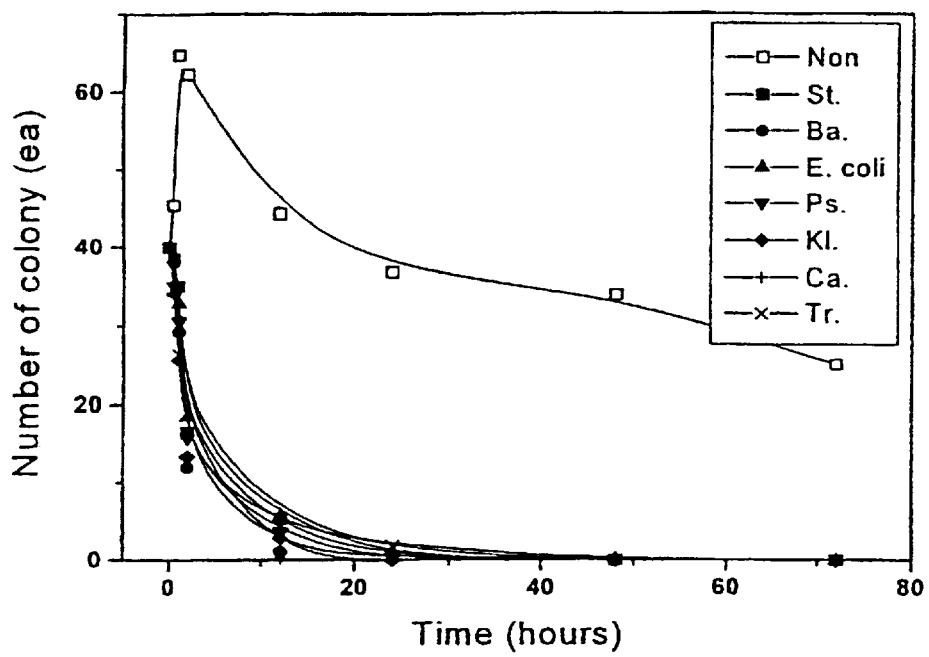
FIG. 1 illustrates comparison of non-treated active carbon with active carbon electro-deposited with Ag—I throughout Example 1 for sterilizing test.

Measurement of BET specific surface area: The amount of adsorption according to increase of concentration is measured with nitrogen as adsorptive gas by taking about 0.2 g specimen under −196° C. of liquid nitrogen and $P/P_0$ (P; partial pressure, $P_0$; saturated vapor pressure) shows linear against partial pressure in the range of 0.05~0.3. From this, specific surface area of BET and volume of micro pore are measured.

Measurement of iodine adsorption capability: According to ASTM D4607, residual concentration of iodine within the solution and amount of adsorptive iodine at each of specimen are measured. From this, the adsorptive capability is decided as iodine adsorption amount when residual concentration is 0.02 N. Before the above measurement, 5 wt % HCl solution, 0.100N sodium thiosulfate solution, 0.100±0.001 N standard iodine solution and 0.100 N iodine acid kalium solution is prepared and used after standardization. 0.1, 0.3, 0.5 and 1.0 g of specimens are put into triangle flask, 10 ml of 5 wt % HCl solution is added into same flask, heated for 30 seconds slowly and then 50 ml of standard iodine solution is added into same flask. Filtrate solution is titrated by 0.100 N sodium thiosulfate, after shaking for 15~20 minutes in the room temperature. Amount of absorptive iodine mg is measured to be titrated until yellow color of iodine is disappeared.

Method of measuring anti-bacteria and sterilizing effect: Testing for the sterilizing and anti-bacteria effect of active carbon electro-deposited with Ag—I is done by Quinn test method. Before the testing, non-treated active carbon and electro-deposited active carbon are prepared and cleaned, and known bacteria are cultured at the room temperature after prepared specimens of non bacteria which have already sterilized in the high temperature and vacuum high-temperature and condition. This test can be used for estimating growth and growth resistance. With these tests, sterilization and anti-bacteria effect are also evaluated throughout observing the number of Colony of bacteria by microscope, which is grown in the non-treated active carbon and electro-deposited active carbon.

TABLE 1

|  | BET Specific surface area ($m^2/g$) | Micropore volume (cc/g) | Iodine adsorptive capability (mg/g) |
| --- | --- | --- | --- |
| Non-treated active carbon | 1560 | 0.76 | 1644 |
| Example 1 | 1548 | 0.75 | 1635 |
| Example 2 | 1540 | 0.73 | 1624 |
| Example 3 | 1542 | 0.75 | 1622 |
| Example 4 | 1549 | 0.75 | 1638 |
| Example 5 | 1545 | 0.76 | 1628 |
| Example 6 | 1544 | 0.75 | 1625 |
| Example 7 | 1540 | 0.72 | 1623 |
| Example 8 | 1548 | 0.74 | 1636 |
| Example 9 | 1542 | 0.72 | 1635 |
| Example 10 | 1033 | 0.81 | 1022 |
| Example 11 | 1045 | 0.82 | 1036 |
| Example 12 | 1038 | 0.81 | 1034 |

Table shows average of each measurement by each example.

Industrial Applicability

In this invention, the adsorptive capability, sterilizing and anti-bacteria effect of active carbon are determined by inherent surface characteristics of active carbon such as specific surface area, pore structure and characteristic of surface element according to plating treatment. Compared with existing methods of impregnating metal elements such as dipping, chemical vapor deposition and add up during manufacturing process, electro-depositing systems like this invention can provide active carbon with high surface activation by the plated element. Improvement of the active carbons adsorption capability without changing its surface structure and its superior anti-bacteria and sterilizing effect against disease-source bacteria and virus provided by the inherent characteristics of silver and iodine. The active carbon of the present invention can be used widely as a filtering material for drinking water and air-conditioning system free of disease-source.

What is claimed is:

1. A method for preparing an active carbon electro-deposited with Ag—I having a sterilizing and anti-bacteria effect comprising:

(a) applying electric current to the active carbon in an Ag plating bath containing Ag salt solution in the plating bath;

(b) washing and drying the active carbon of (a); and (c) applying electric current to the washed and dried active carbon in an Iodine plating bath containing Iodine salt solution.

2. The method according to claim 1, wherein the active carbon electro-deposited with Ag—I has a specific surface area of from 1000 $m^2/g$~1600 $m^2/g$.

3. The method according to claim 1, wherein the Ag salt is $AgNO_3$, $CH_3CO_2Ag$ or AgCN.

4. The method according to claim 1, wherein the concentration of Ag salt is 1~10 wt % and concentration of iodine salt is 5~30 wt % of the plating bath.

5. The method according to claim 1, wherein the Iodine salt is $KIO_3$ or $NaIO_3$.

6. The method according to claim 1, wherein the electric current applied is 1~50 V and 0.1~5 A for 10~120 seconds.

* * * * *

UNITED STATES PATENT AND TRADEMARK OFFICE
CERTIFICATE OF CORRECTION

PATENT NO.     : 6,413,405 B1
DATED          : July 2, 2002
INVENTOR(S)    : Woo Young Jung It is certified that error appears in the above-identified patent and that said Letters Patent is hereby corrected as shown below:

Column 1,
Line 15, "increase the" should read -- increases the --.

Column 2,
Line 19, "10-120" should read -- 10~120 --.

Column 3,
Line 22, "m'/g" should read -- $m^2/g$ --.

Figure 2:
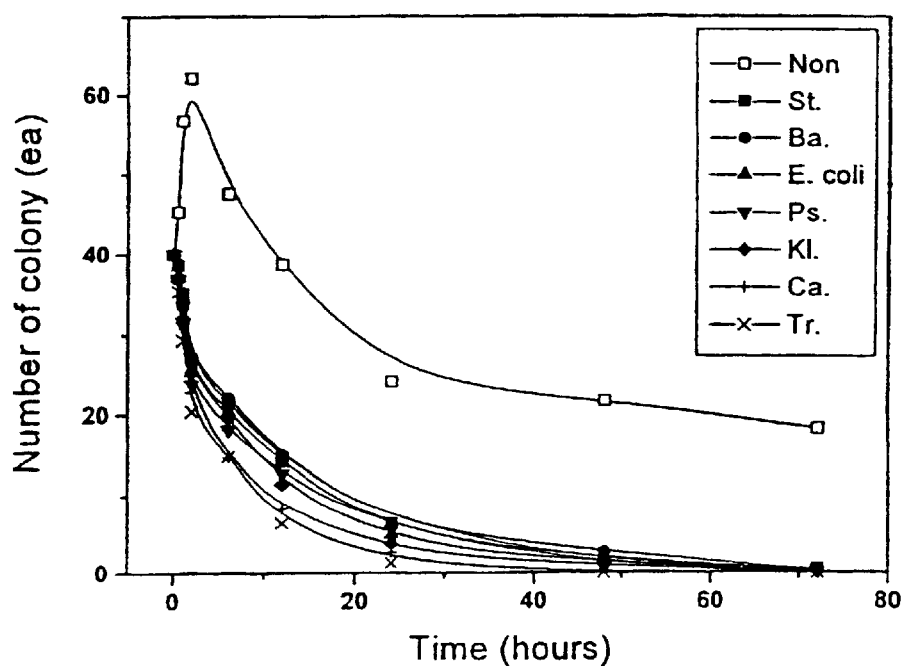
FIG. 2 illustrates comparison of non-treated active carbon with active carbon electro-deposited with Ag—I throughout Example 2 for sterilizing test.
Figure 3:
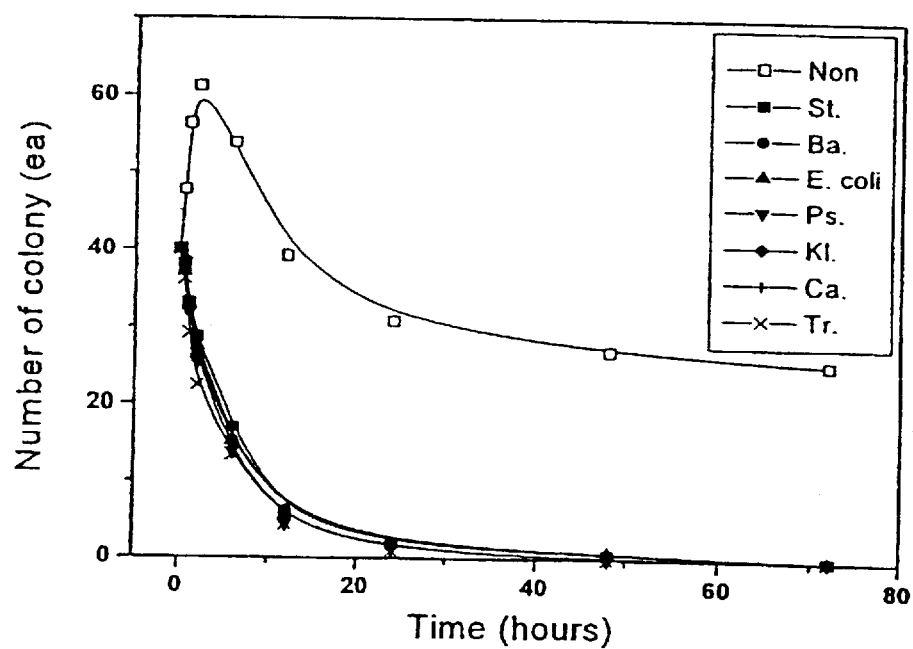
FIG. 3 illustrates comparison of non-treated active carbon with active carbon electro-deposited with Ag—I throughout Example 3 for sterilizing test.
Figure 4:
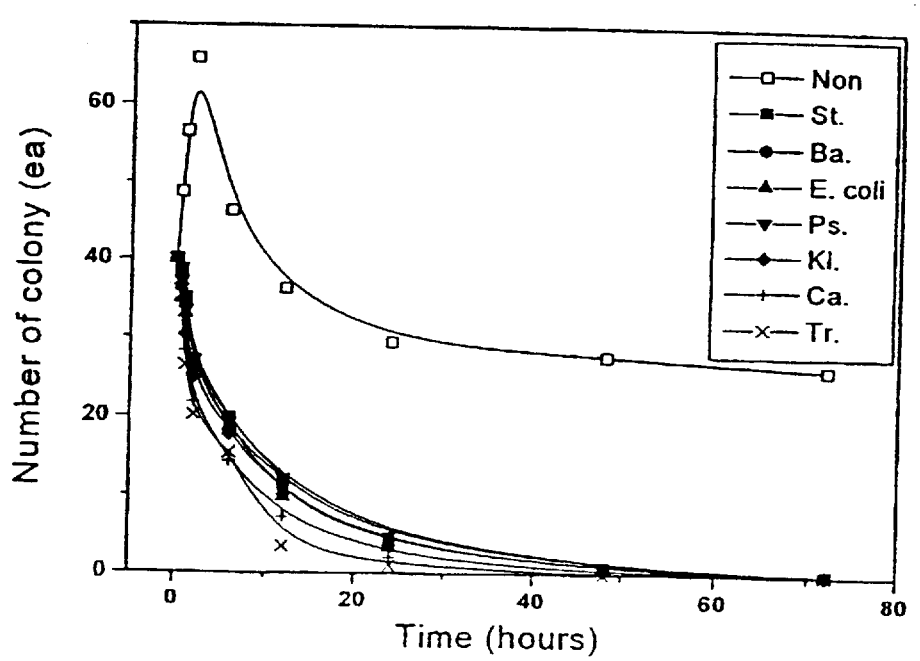
FIG. 4 illustrates comparison of non-treated active carbon with active carbon electro-deposited with Ag—I throughout Example 4 for sterilizing test.
Figure 5:
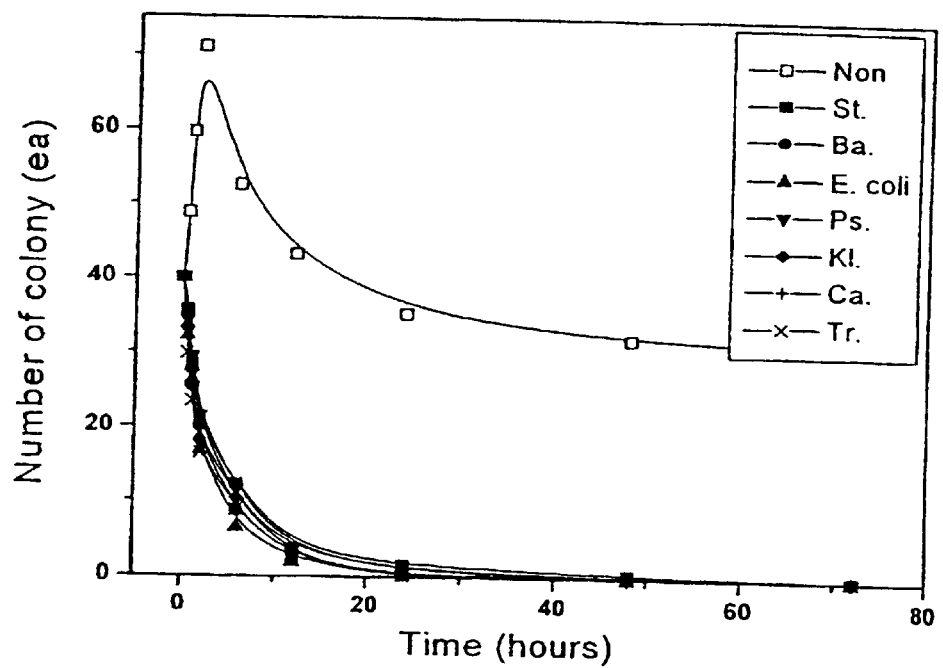
FIG. 5 illustrates comparison of non-treated active carbon with active carbon electro-deposited with Ag—I throughout Example 5 for sterilizing test.
Figure 6:
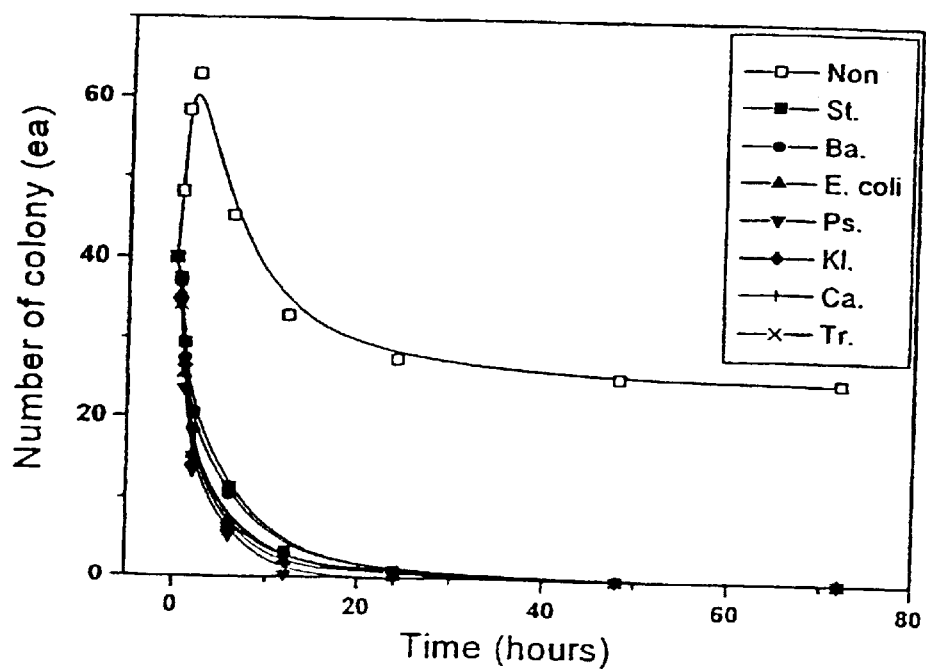
FIG. 6 illustrates comparison of non-treated active carbon with active carbon electro-deposited with Ag—I throughout Example 6 for sterilizing test.
Figure 7:
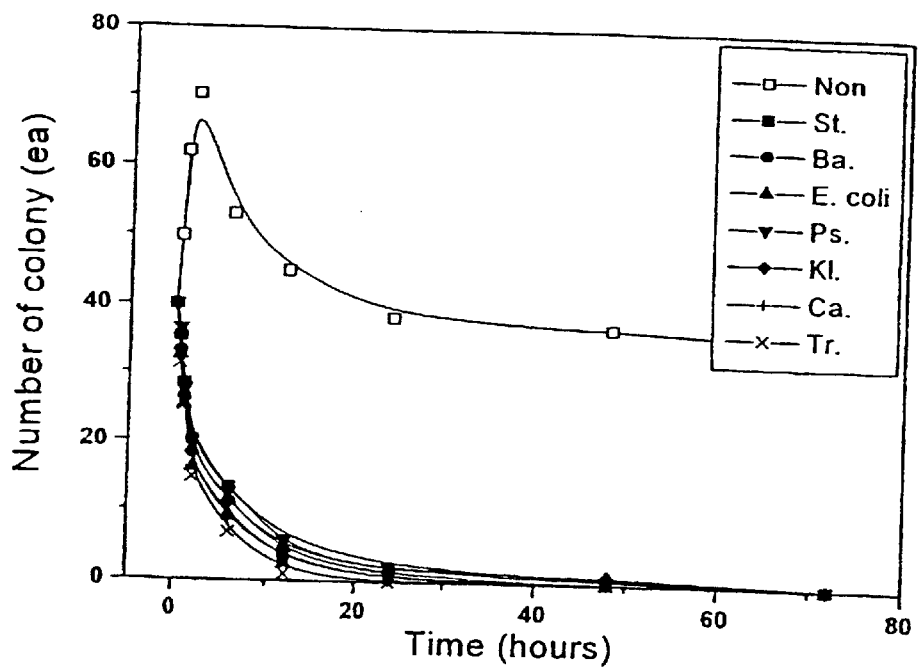
FIG. 7 illustrates comparison of non-treated active carbon with active carbon electro-deposited with Ag—I throughout Example 7 for sterilizing test.
Figure 8:
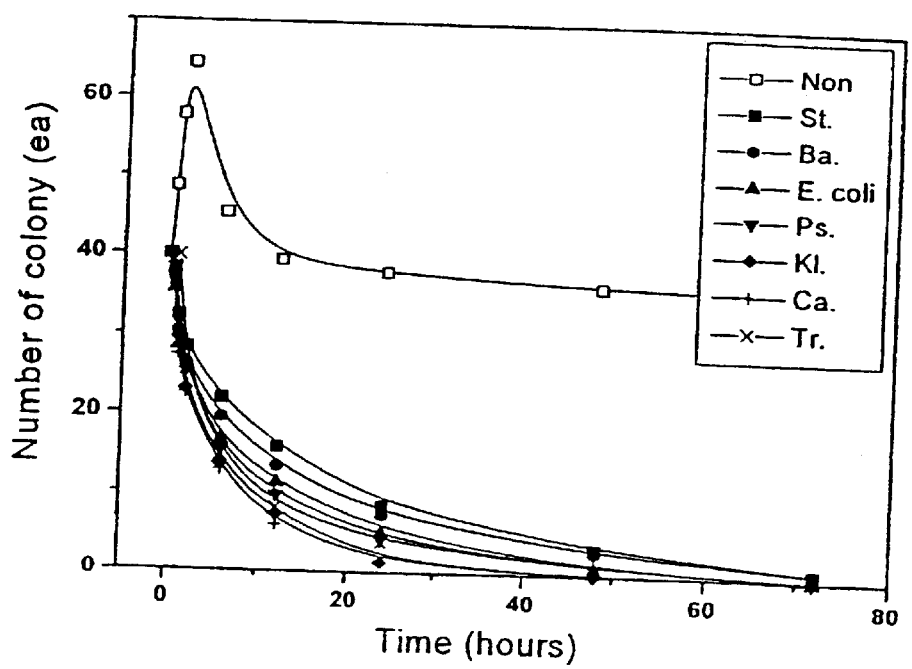
FIG. 8 illustrates comparison of non-treated active carbon with active carbon electro-deposited with Ag—I throughout Example 8 for sterilizing test.
Figure 9:
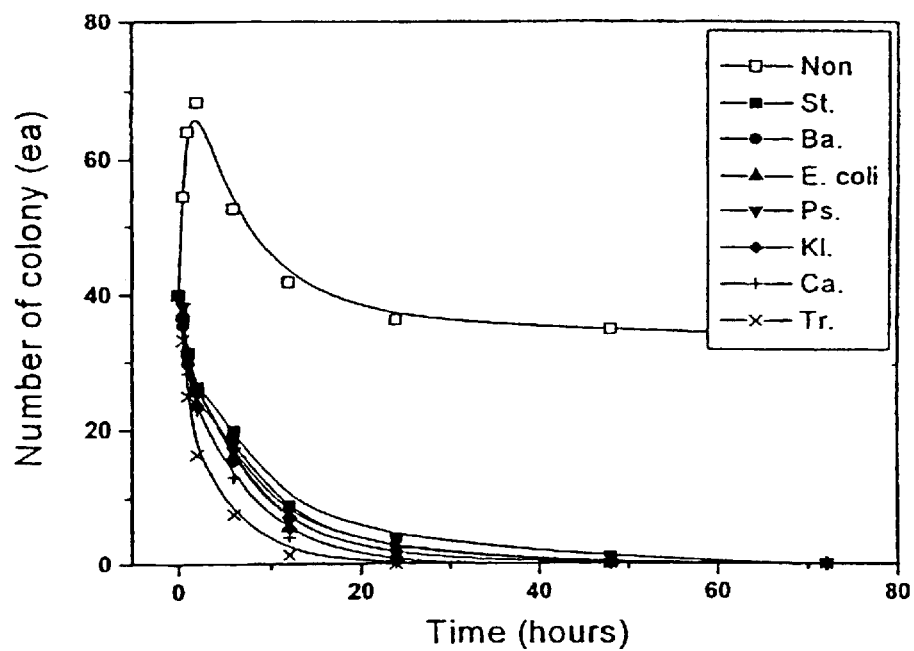
FIG. 9 illustrates comparison of non-treated active carbon with active carbon electro-deposited with Ag—I throughout Example 9 for sterilizing test.
Figure 10:
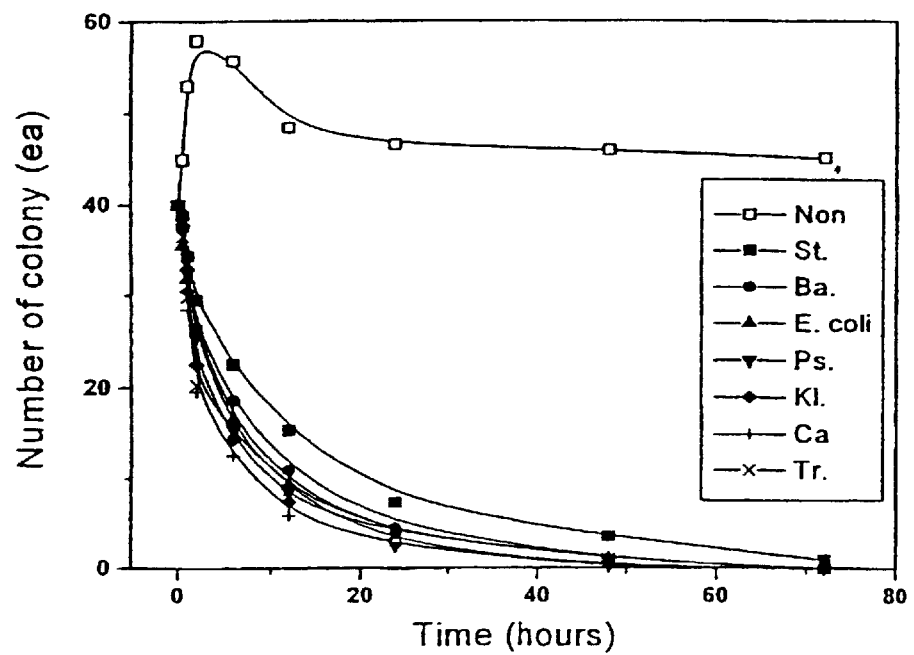
FIG. 10 illustrates comparison of non-treated active carbon with active carbon electro-deposited with Ag—I throughout Example 10 for sterilizing test.
Figure 11:
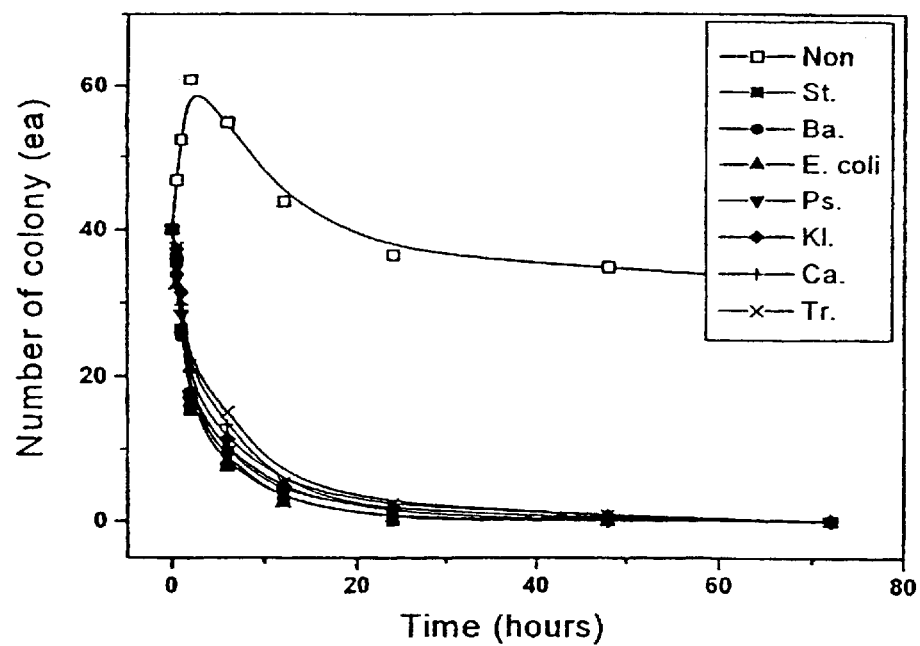
FIG. 11 illustrates comparison of non-treated active carbon with active carbon electro-deposited with Ag—I throughout Example 11 for sterilizing test.
Figure 12:
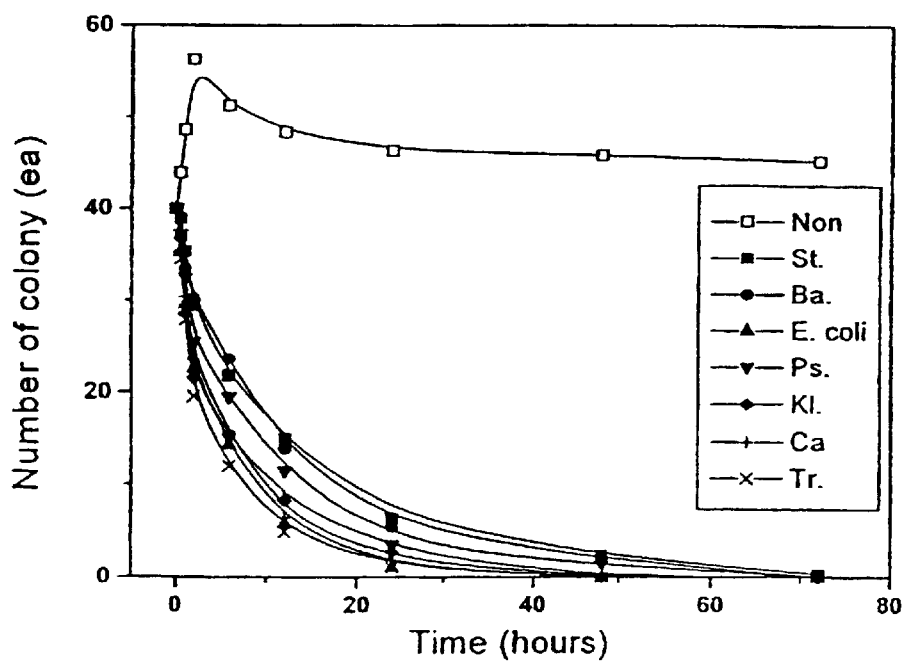
FIG. 12 illustrates comparison of non-treated active carbon with active carbon electro-deposited with Ag—I throughout Example 12 for sterilizing test.

Column 8,
Lines 44-51, delete the following, "Each active carbon electro-deposited with Ag—I system is washed 2 or 3 times and dried at 100°C. for 12 hours and used. Comparison between the active carbon made from the above examples and non-treated active carbon in pore structure, specific surface area and iodine adsorption capability and Quin tests for anti-bacteria and sterilizing are made as follows, and then the results are illustrated at Table 1 and FIGS. 1 to 12." (duplicate text)

Column 10,
Line 23, delete "Industrial Applicability".
Line 37, "virus provided" should read -- virus are provided --.

Signed and Sealed this

Fourth Day of February, 2003

JAMES E. ROGAN
*Director of the United States Patent and Trademark Office*